United States Patent
Urano et al.

(10) Patent No.: US 9,506,876 B2
(45) Date of Patent: Nov. 29, 2016

(54) X-RAY INSPECTION DEVICE, INSPECTION METHOD, AND X-RAY DETECTOR

(71) Applicant: Hitachi High-Technologies Corporation, Minato-ku, Tokyo (JP)

(72) Inventors: Yuta Urano, Tokyo (JP); Toshifumi Honda, Tokyo (JP); Yasuko Aoki, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 161 days.

(21) Appl. No.: 14/371,427

(22) PCT Filed: Dec. 12, 2012

(86) PCT No.: PCT/JP2012/082126
§ 371 (c)(1),
(2) Date: Jul. 9, 2014

(87) PCT Pub. No.: WO2013/118386
PCT Pub. Date: Aug. 15, 2013

(65) Prior Publication Data
US 2014/0328459 A1 Nov. 6, 2014

(30) Foreign Application Priority Data

Feb. 6, 2012 (JP) .................................. 2012-022650

(51) Int. Cl.
*G01N 23/04* (2006.01)
*G01T 1/20* (2006.01)
(Continued)

(52) U.S. Cl.
CPC ............ *G01N 23/04* (2013.01); *G01N 23/043* (2013.01); *G01N 23/16* (2013.01); *G01N 23/18* (2013.01);
(Continued)

(58) Field of Classification Search
CPC ...... G01N 23/04; G01N 23/16; G01N 23/18; G01N 23/043; G01N 2223/642; G01N 2223/643; G01N 2223/646; G01N 2223/652; G01N 2223/6462; G01N 2223/639; G01N 23/02; G01N 23/06; G01T 1/20; G01V 5/0016; G01V 5/0066; G01V 5/0008
See application file for complete search history.

(56) References Cited

U.S. PATENT DOCUMENTS 6,324,249 B1    11/2001  Fazzio
2004/0131140 A1*  7/2004  Bruder .................. A61B 6/032
                                              378/4

(Continued)

FOREIGN PATENT DOCUMENTS

JP    06-317544 A    11/1994
JP    09-072863 A    3/1997

(Continued)

OTHER PUBLICATIONS

Rosenbaum, M., et al., "Calculating Virtual Focal Planes for TDI-Imaging", Signal Processing Algorithms, Architectures, Arrangements, and Applications Conference Proceedings (SPA), IEEE, Sep. 29, 2011, pp. 1-5.

(Continued)

*Primary Examiner* — Hoon Song
(74) *Attorney, Agent, or Firm* — Miles & Stockbridge P.C.

(57) ABSTRACT

The X-ray inspection device includes: an X-ray source with a focal spot size greater than the diameter of a defect for irradiating a sample with X-rays; an X-ray TDI detector arranged near the sample and having long pixels in a direction parallel to the scanning direction of the sample for detecting the X-rays emitted by the X-ray source and passing through the sample as an X-ray transmission image; and a defect-detecting unit for detecting defects based on the X-ray transmission image detected by the X-ray TDI detector.

12 Claims, 8 Drawing Sheets

(51) Int. Cl.
 *G01N 23/16* (2006.01)
 *G01N 23/18* (2006.01)
(52) U.S. Cl.
 CPC ........... *G01T 1/20* (2013.01); *G01N 2223/642* (2013.01); *G01N 2223/643* (2013.01); *G01N 2223/646* (2013.01); *G01N 2223/652* (2013.01)

(56) References Cited

U.S. PATENT DOCUMENTS

| | | | | |
|---|---|---|---|---|
| 2004/0240607 A1* | 12/2004 | Moermond | ............ | G01N 23/04 378/53 |
| 2004/0264635 A1* | 12/2004 | Eberhard | ............... | A61B 6/025 378/22 |
| 2007/0189460 A1* | 8/2007 | Buck | ...................... | G01N 23/04 378/146 |
| 2008/0101549 A1* | 5/2008 | Eliasson | .............. | G01R 31/308 378/207 |
| 2010/0119038 A1* | 5/2010 | Suyama | ................. | G01N 23/04 378/57 |
| 2011/0164729 A1 | 7/2011 | Kikuchi | | |

FOREIGN PATENT DOCUMENTS

| | | |
|---|---|---|
| JP | 11-316197 A | 11/1999 |
| JP | 2009-080030 A | 4/2009 |
| JP | 2010-230559 A | 10/2010 |
| JP | 2010-230572 A | 10/2010 |
| JP | 2011-149701 A | 8/2011 |
| JP | 2011-169777 A | 9/2011 |

OTHER PUBLICATIONS

Extended European Search Report issued Aug. 7, 2015, in European Patent Application No. 12868086.5.

* cited by examiner

ON THE PHOTORECEPTIVE PART

X-RAY INSPECTION DEVICE, INSPECTION METHOD, AND X-RAY DETECTOR

TECHNICAL FIELD

The present invention pertains to an X-ray inspection device irradiating X-rays on a sample and inspecting the sample on the basis of the irradiance distribution of X-rays transmitted through the sample; a detection method; and an X-ray detector used in the X-ray inspection device.

BACKGROUND ART

As background art for the present technical field, there is JP-A-09-72863 (Patent Literature 1), in this publication, there is disclosed (in Claim 1 of the Claims) "a simple high-resolution automatic X-ray transmission inspection device wherein a sample under inspection is transported at a level which is several tens of centimeters in the upward direction from the floor face and characterized by being provided with:
an X-ray source with a focal size diameter of 50 µm or more;
a shielded box in which, together with an X-ray source being disposed in the upper part, there is disposed an imaging face imaging the picture of a sample under inspection on the lower and inner side compared to an inspected sample carry-in/carry-out aperture; and
a raising and lowering stage having an inspected sample horizontal transfer function and going up and down between the height level of said carry-in/carry-out aperture and the height level of said imaging face in the imaging place inside said shielded box, going down to the upper side inspection level of said imaging face while supporting a sample under inspection received in said carry-in aperture and going up to the height level of the carry-out aperture while supporting the imaged sample under inspection." and it is reported that, by means hereof, the provision of "a compact simple high-resolution automatic X-ray transmission inspection device with which print substrate images can be obtained at a low cost and with excellent resolution and the maintenance and exchange of the X-ray source can be performed readily" becomes possible.

CITATION LIST

Patent Literature

PATENT LITERATURE 1: JP-A-09-72863

SUMMARY OF INVENTION

Technical Problem

In the inspection of microscopic metal contaminants included in the electrode material of a lithium ion accumulator, it is demanded to inspect microscopic metal objects, 50 µm or smaller, at high speed. Since, in the manufacturing process of the electrodes, sheet-shaped electrode material is continuously transported at a high speed, a speed of 500 mm/s or more, by means of roll transport, it is necessary, for in-line inspection, to inspect continuously at a sample scanning speed of 500 mm/s or more.

In order to inspect microscopic objects in an X-ray inspection in which X-rays are irradiated on a sample and the sample is inspected on the basis of the irradiance distribution of X-rays transmitted through the sample, it is necessary to obtain transmission images with high resolution and obtain X-ray transmission images based on sufficiently great X-ray fluence. Here, the expression "X-ray fluence" refers to the product of the irradiance of X-rays irradiated on the sample and the accumulated time (exposure time) of the detector.

The fact that the former is necessary is because, in the case where the resolution is low as compared to the size of the objects, the images end up becoming blurred and the contrast of the images of the objects is diminished.

The fact that the latter is necessary is because, in the case where the X-ray fluence is insufficient, shot noise becomes relatively great with respect to the contrast of the images of the objects and, due to the fact that the S/N (signal-to-noise) ratio of the images diminishes, it becomes difficult to distinguish the objects. Here, "shot noise" designates photon shot noise or what is also called quantum noise and, in the case where the ratio accounting for the shot noise component within the noise of the images is great, the S/N ratio of the images is improved by increasing the X-ray fluence, in proportion to the square root of the X-ray fluence.

In order to obtain high-resolution X-ray transmission images, there is a method of using an X-ray source with small focal spot size such as a microfocus X-ray tube and making the distance between the X-ray source and the camera great as compared to the distance between the X-ray source and the sample. However, since an X-ray source with a small focal spot size cannot obtain high output, the S/N ratio of the images diminishes due to the insufficiency of the X-ray fluence. In particular, since the accumulation time becomes shorter in the case of carrying out high-speed detection, this problem becomes noticeable.

In order to obtain high X-ray fluence, there is a method of using a high-output X-ray source or alternatively gaining accumulation time using an X-ray camera of the TDI (Time Delay Integration) type. However, as for the former, since an X-ray source with a large focal spot size is necessary, there is the problem that it is not compatible with high-resolution image acquisition. As for the latter, there is a need to synchronize the line rate of the IDE camera with the sample scanning speed, but since there is an upper limit to the line rates of commercially available TDI cameras, there is the problem that it is not possible to accommodate very high sample scanning speeds. E.g., for an X-ray TDI camera with an upper-limit line rate of approximately 2 kHz, in the case of pixel dimensions of 50 µm, the upper-limit sample transport speed that can be accommodated is 100 mm/s.

In aforementioned Patent Literature 1, there is reported an automatic X-ray transmission inspection device with high resolution. However, as for the device of Patent Literature 1, there is reported "a raising and lowering stage having an inspected sample horizontal transfer function and going up and down between the height level of said carry-in/carry-out aperture and the height level of said imaging face in the imaging place inside said 215 shielded box, going down to the upper side inspection level of said imaging face while supporting a sample under inspection received in said carry-in aperture and going up to the height level of the carry-out aperture while supporting the imaged sample under inspection" as a configuration for acquiring high-resolution images, but no report regarding the necessity of increasing X-ray fluence is made. Also, no report is made regarding the inspection method of a sample transported with high speed.

Solution to Problem

In order to resolve the aforementioned problem, there is e.g. adopted a configuration set out in the Claims.

As for the present application, there are included several means of solving the aforementioned problem, but if one were to cite an example thereof, it is characterized by having:

an X-ray source irradiating X-rays on a sample and having a focal spot size greater than the diameter of a defect;

an X-ray TDI detector detecting, as an X-ray transmission image, X-rays irradiated by means of the aforementioned X-ray source and transmitted through the aforementioned sample, having pixels that are longer in a direction parallel to the scanning direction of the aforementioned sample, and being arranged adjacent to the aforementioned sample; and a defect detection part detecting defects on the basis of the X-ray transmission image detected by means of the aforementioned X-ray TDI detector.

Advantageous Effects of Invention

According to the present invention, it is possible, by obtaining a high-resolution X-ray transmission image with sufficiently great X-ray fluence, to detect microscopic defects.

Problems, configurations, and effects other than those mentioned above will become clear from the description of the embodiment below.

DESCRIPTION OF EMBODIMENTS

In the present embodiment, there will be given a description of an example of an X-ray inspection device irradiating X-rays on a sample and inspecting the sample on the basis of the irradiance distribution of X-rays transmitted through the sample.

Figure 1:
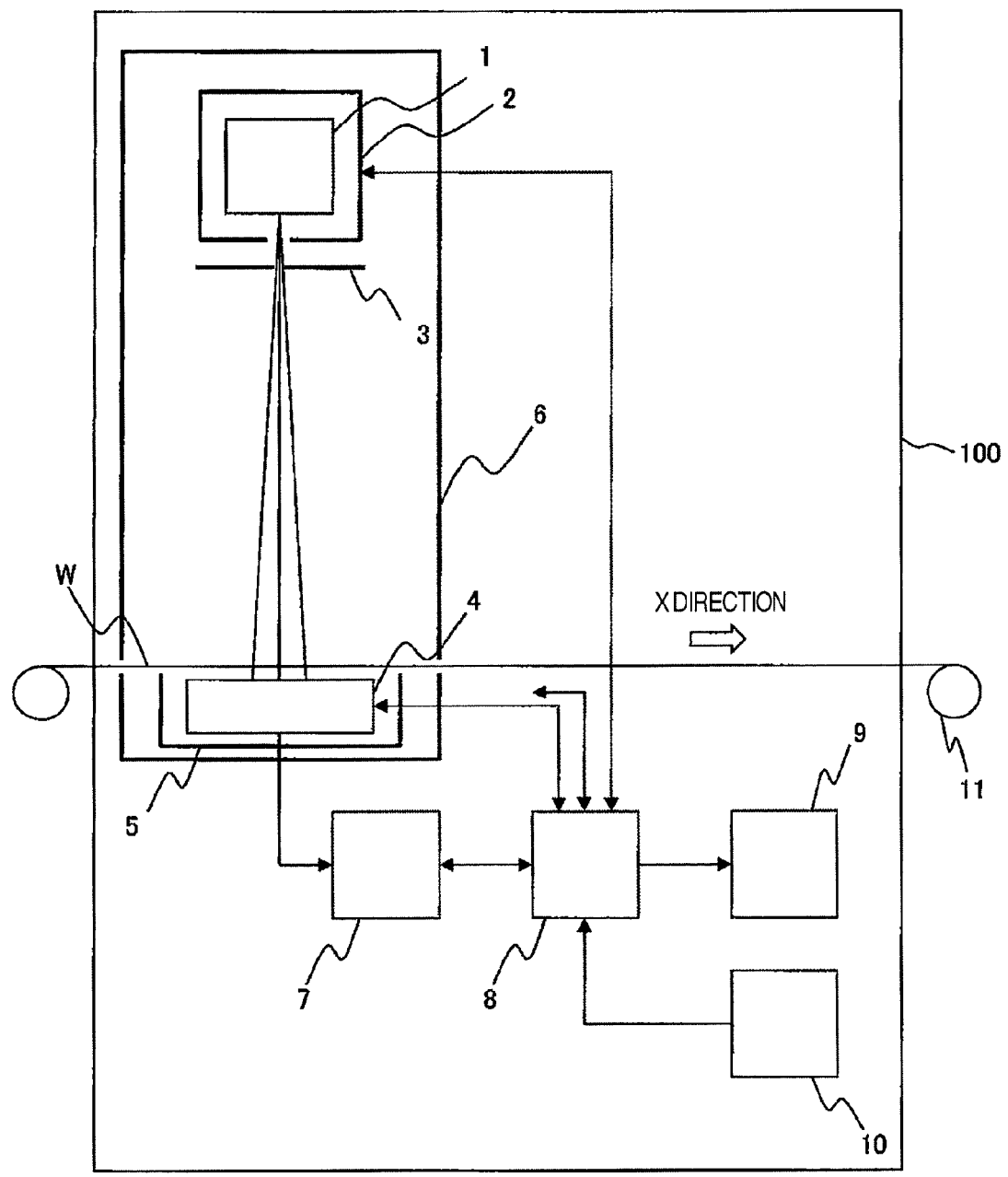
FIG. 1 is a block diagram for describing the configuration of an X-ray detection device related to the present invention.

FIG. 1 is an example of a block diagram of an X-ray inspection device of the present embodiment.

X-ray inspection device 100 has an X-ray source 1, a radiation source shielding part 2, a radiation source slit 3, an X-ray TDI camera 4, a direct light shielding part 5, a device cover 6, a defect judgment part 7, a control part 8, and a display part 9.

X-ray source 1 irradiates X-rays toward a sample W. The shape of the X-ray irradiation region on the sample, due to X-ray source 1, is restricted by means of radiation source slit 3. Radiation source shielding part 2 shields X-rays directed to other places than the irradiation region on the sample. By means of radiation source shielding part 2 and radiation source slit 3, the amount of leakage of X-rays not needed for the inspection is reduced, so the safety of X-ray inspection device 100 is improved.

The X-rays irradiated on sample W are transmitted through sample W and are detected as an X-ray transmission image by means of X-ray TDI camera 4. By using TDI camera 4 as a detector, it is possible to acquire X-ray transmission images uninterruptedly of a continuously transported sample W. Also, compared to the case of using a normal X-ray line camera, it is possible to obtain accumulation time that is greater only by the extent of the number of TDI stages, and by increasing the X-ray fluence, images with a high S/N ratio are obtained, so detection sensitivity is improved.

Direct light shielding part 5 shields X-rays transmitted through sample W and TDI camera 4 and is a part for preventing X-rays from leaking to the outside of the device. Device cover 6, together with shielding the X-ray component that was too much to shield in radiation source shielding part 2, radiation source slit 3, and direct light shielding part 5 as well as the reflected/scattered X-ray component, is a part for separating the space in which X-rays are irradiated and preventing a hand, or the like, of a human being from entering into the same space. In the case where radiation source shielding part 2, radiation source slit 3, direct light shielding part 5, or device cover 6 is not installed in accordance with prescribed conditions, an interlock is operated and the X-ray irradiation due to radiation source 1 is halted. By means of the aforementioned configuration, X-ray radiation exposure of device operators and the like is avoided, so the safety of X-ray inspection device 100 is ensured.

In FIG. 1, there was shown an arrangement in which X-ray source 1 is placed above sample W and X-ray TDI camera 4 is placed below sample W, but in the case where the distance from the face of the floor where X-ray inspection device 100 is installed to sample W is long and it is possible to ensure enough space below sample W, it is acceptable, in order to make the external form of X-ray inspection device 100 compact, to install X-ray source 1 below sample W and to install X-ray TDI camera 4 above sample W. Also, defect judgment part 7, control part 8, or display part 9 may be installed inside device cover 6.

Defect judgment part 7 distinguishes defects that are present in the sample on the basis of X-ray transmission images detected with X-ray TDI camera 4, and outputs the presence or absence thereof and the number present, location, or size. Here, the term "defect" refers to a primary factor that may cause the reliability of a finished lithium ion accumulator product to diminish in the electrode material of a lithium ion accumulator and includes e.g. microscopic metal contaminants included in positive electrode material, negative electrode material, a current collector, or a separator of a lithium ion accumulator or a vacancy or coating defect in positive electrode material, negative electrode material, or a separator thereof.

In the inspection of microscopic metal contaminants included in positive electrode material of a lithium ion accumulator, fixed pattern noise of X-ray TDI camera 4, randomly generated shot noise, as well as thickness irregularities, density irregularities, and the like, of the active material of the sheet-shaped positive electrode become background noise. With respect to the detected images, there is carried out filter processing attenuating background noise and enhancing the defect signal due to microscopic metal contaminants and the like, and with respect to post-filter images, defects such as microscopic metal contaminants are detected by setting a threshold level at which the component of residual noise is substantially not detected and judging portions exceeding the threshold level to be defects. In the case where microscopic metal contaminants are adhering to the positive electrode, or metal components constituted by elements that are heavier than the positive electrode material are embedded in the interior of the positive electrode material, the same appear as defect signals that are darker than the background in the X-ray transmission image. In the case where metal components constituted by elements that are lighter than the positive electrode material are embedded in the interior of the positive electrode material, or in the case where there are positive electrode material coating leaks and vacancies, the same appear as defect signals that are brighter than the background in the X-ray transmission image. The center (the position where the luminosity difference with the background is at a maximum or the center-of-gravity position of the luminosity difference) of the spatial spread of the luminosity of the defect part is measured as the defect position. Further, the size of the defect is measured from the luminosity difference with the background of the defect part and the spatial spread of the luminosity. In order to enable checking the aforementioned defect judgment results after inspection, the defect image including the defect part and the surrounding background is saved in memory incorporated in defect judgment part 7 or control part 8.

Control part 8 receives signals from an input part 10 or each of the aforementioned constituent components and carries out parameter setting and control of X-ray source 1, X-ray TDI camera 4, and defect judgment part 7. The parameter setting values, states, inspection conditions, and defect judgment results (number of defects, positions, defect dimensions, and defect images) of each of the aforementioned constituent parts are displayed in display part 9.

In input part 10, input such as parameter setting values or inspection conditions of each constituent requirement from the exterior such as a user is received and sent to control part 8.

By means of transport system 11, a sample W subject to inspection is transported and scanned. The line rate of X-ray TDI camera 4 is set to match the speed of sample scanning due to transport system 11, so imaging synchronized with the scanning speed is carried out. Transport system 11 outputs information needed for the timing synchronization of X-ray TDI camera 4, such as transport speed or transport distance, to control part 8. E.g., in the case where X-ray inspection device 100 is installed in an environment where, in the sample manufacturing process or the like, the sample is already substantially transported with a fixed speed, there is no need for X-ray inspection device 100 itself to have a transport system 11, so the transport system already installed in the manufacturing process or the like is used in combination, and X-ray TDI camera 4 may be set and operated in synchronization herewith. In this case, as the need arises, output of the transport system of the sample manufacturing process or the like, or the position measurement value obtained by measurement by means of an encoder, or the speed measurement value obtained by measurement by means of a speed indicator is input to the control part as information used for synchronization and used.

Figure 2:
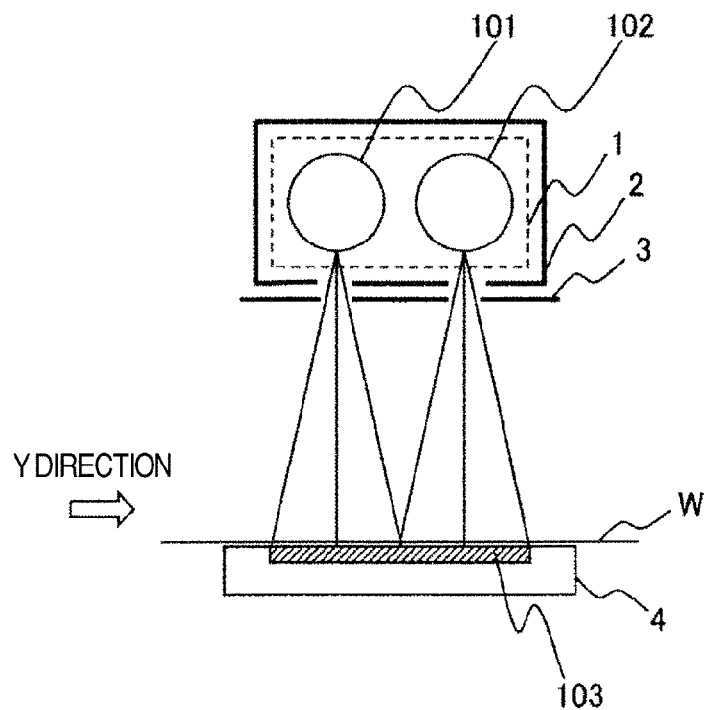
FIG. 2 is a block diagram describing an X-ray source related to the present invention.

FIG. 2 is a block diagram describing the X-ray source of the present embodiment.

Figure 6:
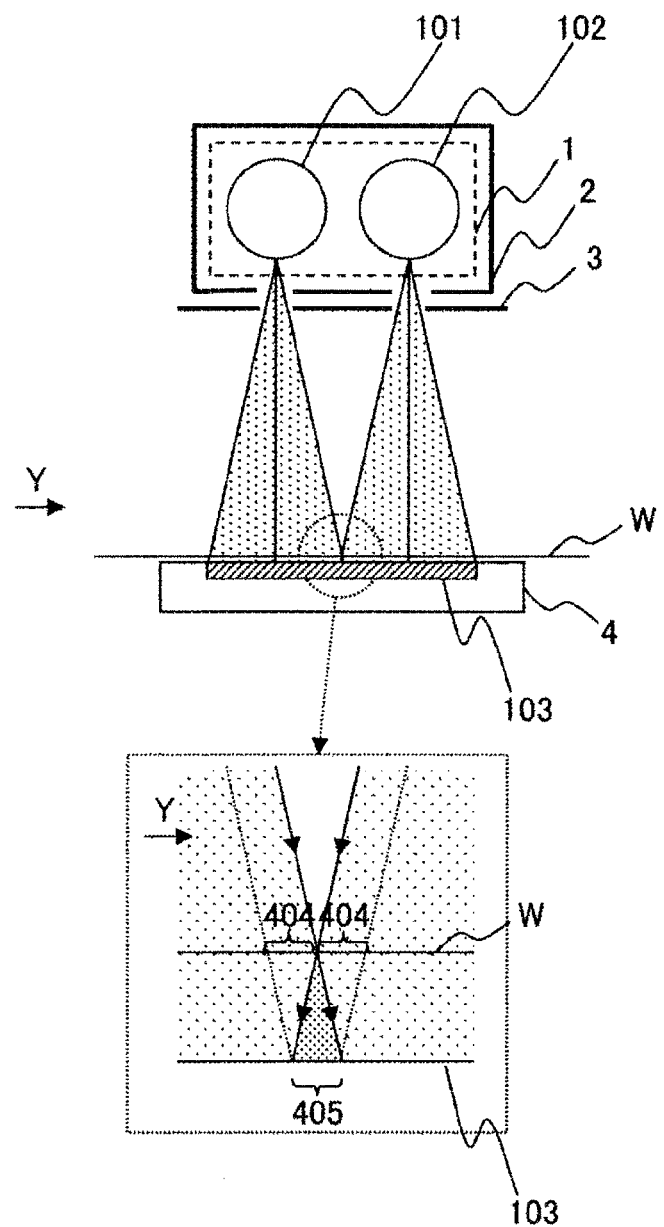
FIG. 6 is a diagram describing the duplication of images due to a plurality of X-ray tubes related to the present invention.
Figure 7:
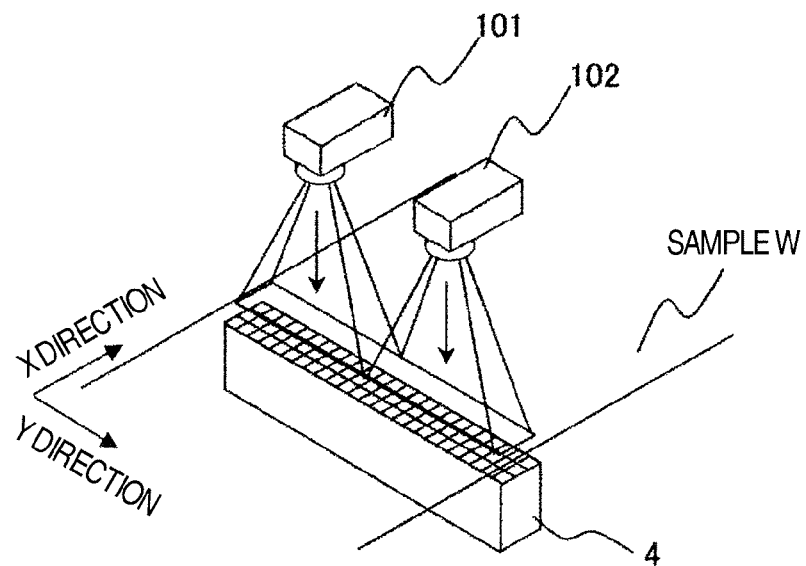
FIG. 7 is a diagram describing the arrangement of light source parts and TDI cameras, related to the present invention.

X-ray source 1 has a plurality of X-ray tubes. In FIG. 2, and FIG. 6 and FIG. 7 to be subsequently described, there was illustrated an example in which X-ray source 1 has two X-ray tubes 101 and 102, but it is acceptable to use three or more X-ray tubes in order to augment the X-ray fluence more. Each of X-ray tubes 10 and 102 irradiate on sample W in mutually different regions. In order that irradiation regions on sample W do not overlap, a radiation source slit 3 is installed and adjusted. The X-rays transmitted through the regions on sample W that are irradiated by X-ray tubes 101 and 102 are incident on photoreceptive part 103 of X-ray TDI camera 4 and are detected. By lining up N X-ray tubes and utilizing the same, the length of the region irradiated by one X-ray tube gets multiplied by 1/N, and the distance between one X-ray tube and the sample gets multiplied by 1/N. Since the X-ray irradiance is inversely proportional to the square of the distance from the X-ray tubes, the X-ray irradiance supplied per unit area on the sample is increased by the square of N. In this way, it is possible to increase the X-ray fluence.

FIG. 7 is a diagram describing the arrangement of the light source part and the TDI camera of this embodiment. The sample W scanning direction is taken to be the x direction and the direction perpendicular thereto is taken to be the y direction. X-ray TDI camera 4 is set and adjusted so that the x direction is the TDI accumulation direction and the y direction is the longitudinal direction. The plurality of X-ray tubes (101, 102) that X-ray source 1 has are arranged in order along the y direction.

Figure 3:
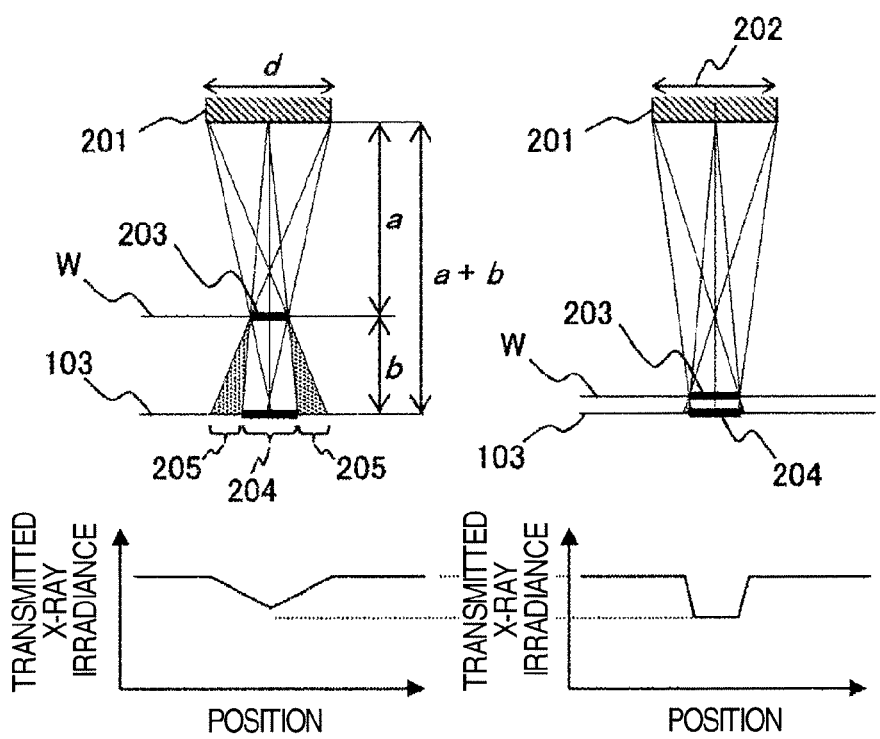
FIG. 3 is a diagram describing the positional relationship of an X-ray source, an object subject to inspection and a TDI camera that are related to the present invention.

FIG. 3 is a diagram describing the positional relationship of an X-ray source, an object subject to inspection, and a TDI camera.

In the interior of an X-ray tube included in an X-ray source, the region where the X-rays are generated is called a focal spot. Ref 201 of FIG. 3 indicates the focal spot region of an X-ray tube. Focal spot region 201 has a finite size. Here, the focal spot size is taken to be disc, the focal spot size disc being set to be greater than a defect diameter. E.g., in an X-ray tube with a focal spot size d=0.4 mm, there can be obtained a continuous output of 200 W and in an X-ray tube with d=1 mm, there can be obtained a continuous output of 1000 W. The X-rays emitted from focal spot region 201 are transmitted through sample face W and an image 204 of a microscopic object 203 in the photoreceptive part. At this point, there is generated an image blur 205 corresponding to focal spot size d on both flanks of image 204. As shown in the right-side diagram of FIG. 3, by making photoreceptive part 103 approach sample face W, it is possible to reduce the size of the blur with respect to the image of the microscopic object. If the size of the blur is large with respect to the size of the image of the object, the detection sensitivity diminishes since the contrast of the microscopic object in the transmitted X-ray irradiance distribution detected with photoreceptive part 103 diminishes.

From a geometric calculation, the size of blur 205 on the photoreceptive part is expressed as bd/a, using a focal spot size d, a radiation source—sample distance a, and a sample—photoreceptive part distance b. Since the image on the sample is expanded by an expansion factor (a+b)/a on the photoreceptive part, the size of blur 205 converted into the dimensions on the sample can be found as bd/(a+b).

Figure 4:
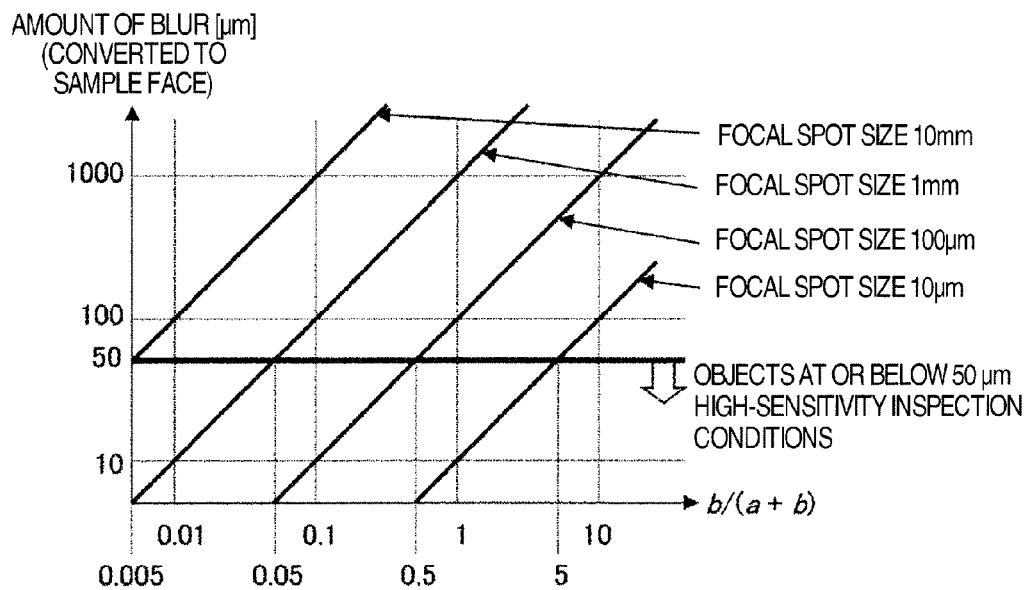
FIG. 4 is a diagram describing the positional relationship and the relationship with the amount of image blurring, of an X-ray source, an object subject to inspection and a TDI camera that are related to the present invention.

FIG. 4 is a diagram describing the positional relationship and the relationship with the amount of blurring, of a light source part, an object subject to inspection and a TDI camera of the present embodiment. On the basis of the aforementioned formula, the ratio of the sample—photoreceptive part distance b to the radiation source—photoreceptive part distance (a+b) is shown on the abscissa axis and the amount of blurs converted to the sample face is obtained, and the amount of blur for each focal spot size is shown on the ordinate axis.

To detect material objects of 50 μm or less with high sensitivity, it is effective to restrain the quantity of blurs to those at or below 50 μm. E.g., in the inspection of microscopic metal contaminants included in the positive electrode material of a lithium ion accumulator, the thickness of the positive electrode material subject to inspection is on the order of 200 μm. In this case, it is possible to make the sample—photoreceptive part distance b approach the order of 1 mm. E.g., in the case of using an X-ray TDI camera 4 with a length of 300 mm in the y direction and four X-ray tubes whose angle of irradiation is 30°, the radiation source—sample distance a becomes 140 mm. At this point, the size of blur 205, converted to dimensions on the sample, becomes d/140, so even if there is used a high-output X-ray source with a large focal spot size, on the order of 5 mm, the blur can be restrained down to the order of 36 μm.

In the case of lining up a plurality of X-ray tubes, the extent to which the distance between the X-ray tube and the sample becomes shorter has a tendency to enlarge the size of blur 205, converted to dimensions on the sample, but particularly in the case where, as mentioned above, the sample subject to inspection is thin, e.g. 1 mm or less, the sample—photoreceptive part distance b can be compressed to the order of 1 mm, so it is possible to ensure a sufficiently high resolution.

Figure 5:
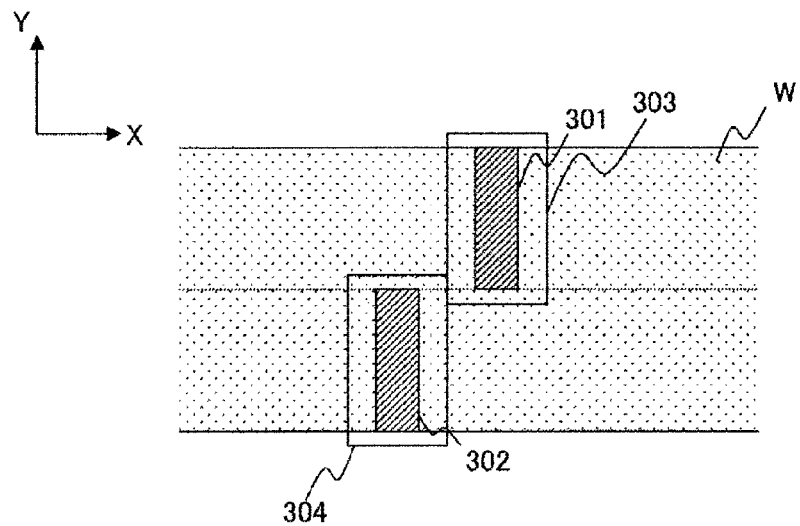
FIG. 5 is a block diagram describing a configuration example in which a plurality of TDI cameras related to the present invention are lined up.

FIG. 5 is a block diagram describing a configuration example of lining up a plurality of TDI cameras.

By lining up plurally X-ray optical systems having a X-ray source 1, a radiation source shielding part 2, a radiation source slit 3, and a TDI camera 4 in the y direction, it is possible to inspect samples with a large width. By lining up a plurality of photoreceptive parts 301, 302 relative to the y direction (the width direction of the sample) without allowing any gaps while sliding a plurality of TDI cameras 303, 304 in the x direction so that the same do not interfere mechanically, it is possible to eliminate any misses in the regions subject to inspection. In FIG. 5, there was illustrated an example in which two were lined up, but it is acceptable to line up three or more.

FIG. 6 is a diagram describing the duplication of images due to a plurality of X-ray tubes.

If sample face W is covered without any gap by means of a plurality of X-ray tubes 101, 102, it is detected, relative to the y direction, that the images of a part of the regions, near the boundary of the it radiation regions of each of the X-ray tubes (regions 404), overlap on the photoreceptive part (region 405). Defect judgment processing corresponding to image overlap is carried out in defect judgment part 7 regarding overlap region 405.

As an example of image processing corresponding to regions in which images overlap, there is the method of raising the defect judgment threshold values only in the overlap region. As for the overlap region, since the background noise of two image portions that are not mutually correlated is superimposed, the noise increases by √2 with respect to regions that do not overlap. Accordingly, by setting the defect judgment threshold value √2 times higher in overlap regions only, it is possible to detect overlap region defects while avoiding erroneous detection resulting from the increase of noise in overlap regions.

The closer to perpendicular that the X-ray incidence angle on the boundary or the shorter the sample—photoreceptive part distance is, the smaller the overlap region becomes. In order to make the overlap region small, it is e.g. effective to use an X-ray tube with a small (e.g. 30° or less) angle of irradiation (the angle of spread of the X-ray beam emitted from an X-ray tube) or, particularly in the case of a small-thickness sample, to reduce the sample—photoreceptive part distance (e.g. b<1 mm), or to increase the number of lined up X-ray tubes and narrow the irradiation region covered by one X-ray tube, or the like.

Figure 8:
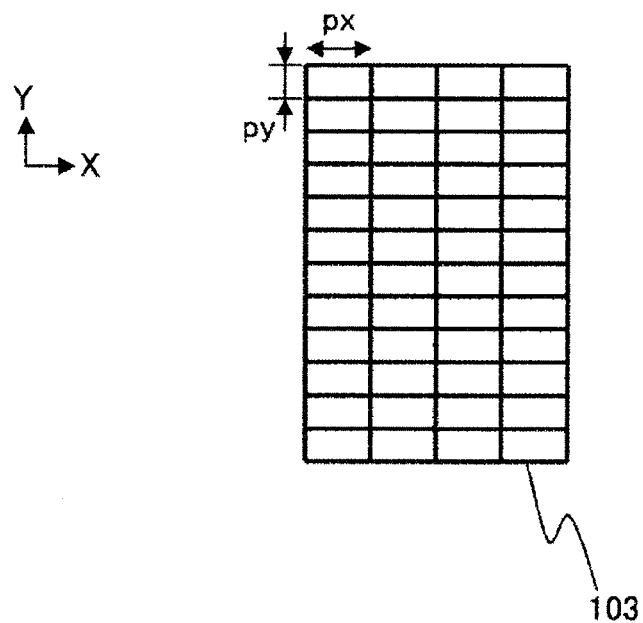
FIG. 8 is a diagram describing an X-ray TDI camera having flat pixels, related to the present invention.

FIG. 8 is a diagram describing an X-ray TDI camera having flat pixels.

As for X-ray TDI camera 4, there is a need to synchronize the sample scanning speed and the imaging frequency (line rate) in order to correctly carry out TDI accumulation. In the case of not synchronizing, inspection sensitivity diminishes since the obtained image is blurred and spread in the x direction. The line rate fL for synchronizing is expressed as fL=M×vx/px, using the pixel size px in the inspected sample scanning speed of the X-ray TDI camera, the sample scanning speed vx, and the image expansion rate M of the X-ray optical system. In the case where sample scanning speed vx is high, there is the problem that synchronized imaging becomes difficult, due to the upper-limit constraint of the line rate of the TDI camera.

As for the aforementioned optical system in which sample W is made to approach the photoreceptive part, since the image expansion rate M thereof is kept low (close to 1), it is possible to restrain the line rate needed for synchronization to be low, so it is effective for carry out high-speed inspection for which the sample scanning speed vx is high.

Also, by enlarging pixel size px in the TDI scanning direction, the line rate needed for synchronization can be reduced, so a response to high-speed inspection becomes possible. The fact of enlarging the pixel size is related with a reduction in sensitivity, since the resolution of detected images diminishes, but by keeping the pixel size small in the y direction and enlarging the pixel size only in the x direction, it becomes possible to carry out high-speed scanning while restraining the reduction in sensitivity due to the resolution decrease to the minimum required.

E.g., in the case of using a TDI camera with a line rate of 2 kHz and with the conditions that px=400 μm, py=50 μm, M=1, it is possible to carry out scanning with a sample scanning speed vx of 800 mm/s. Also, in the case of using a TDI camera with a line rate of 8 kHz and with the conditions that px=100 μm, py=50 μm, M=1, it is possible to carry out scanning with a sample scanning speed vx of 800 mm/s.

If a normal TDI camera with square pixels is made to operate binning only in the x direction, it is possible to use it as a TDI camera for which the aforementioned pixel size in the x direction is greater compared to the pixel size in the y direction. By making a TDI camera with square pixels having a pixel size of 50 μm operate binning for each eight pixels in the x direction, the same operates as a TDI camera with px=400 μm and py=50 μm. By making it operate binning for each two pixels, it operates as a TDI camera with px=100 μm and py=50 μm.

As for the method of creating flat pixels by performing N-pixel binning in the x direction, there is the advantage that it is difficult for signal saturation to occur, even with conditions under which the X-ray fluence is unusually great, since the amount of maximum saturation charge of the TDI camera increases due to binning.

Figure 9:
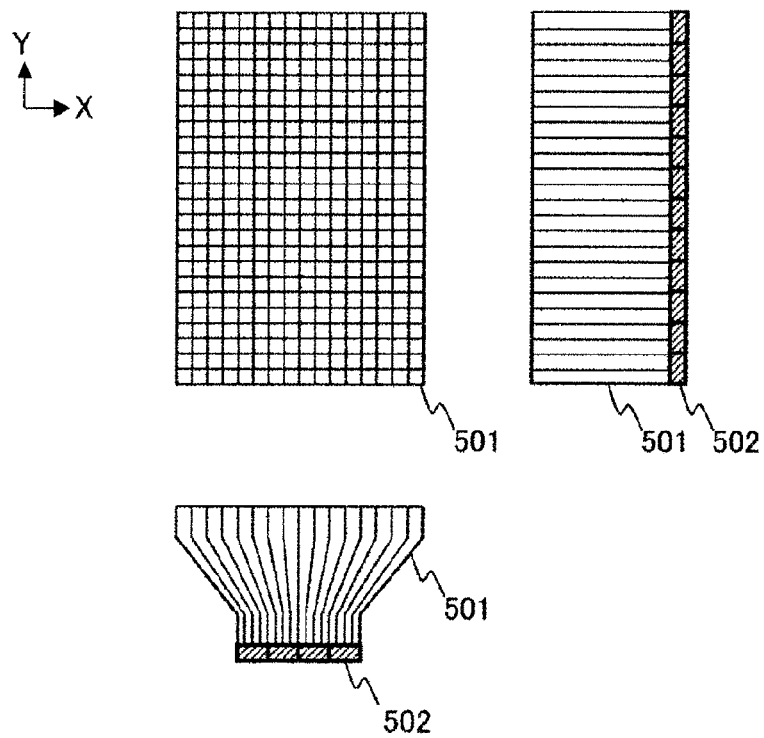
FIG. 9 is a diagram describing another embodiment of an X-ray TDI camera having flat pixels, related to the present invention.

FIG. 9 is a diagram describing another embodiment of an X-ray IDE camera having flat pixels.

An X-ray TDI camera has a configuration in which a scintillator is combined by a fiber optic plate with a TDI camera for visible light. Normally, a fiber optic plate has the function of transferring an image converted into light by the scintillator without carrying out an image transformation or the like, and with the same size, to a IDE camera for visible light. By using an asymmetric fiber optic plate 501, such as one shown in FIG. 9 compressing the x direction to 1/N with respect to the y direction or such as one expanding the y direction N times with respect to the x direction, and combining a scintillator and a square-pixel TDI camera, there is configured an X-ray TDI camera having flat pixels that are longer in the x direction. As an asymmetric fiber optic plate 501, a tapered fiber optic plate is used.

Also, as for the asymmetric fiber optic plate, it is possible to make a substitution with one that transforms and transfers visible tight images with different magnifications lengthwise and breadthwise. E.g., by means of an image formation optical system with different magnifications in the x direction and the y direction and having the combination of a cylindrical lens, an aspherical lens, a spherical lens, and the like, there may be formed an image of the output face of the scintillator on a photoreceptive part 502 of a TDI camera for visible light.

As against the fact that the number of TDI accumulation stages diminishes to 1/N by means of binning in the method of creating flat pixels by performing N-pixel binning in the x direction, there is the advantage that it is possible for the method of creating flat pixels using an asymmetric fiber optic plate to gain more X-ray fluence even under the same X-ray irradiation conditions, since the original number of TDI accumulation stages of the TDI camera is maintained.

Figure 10:
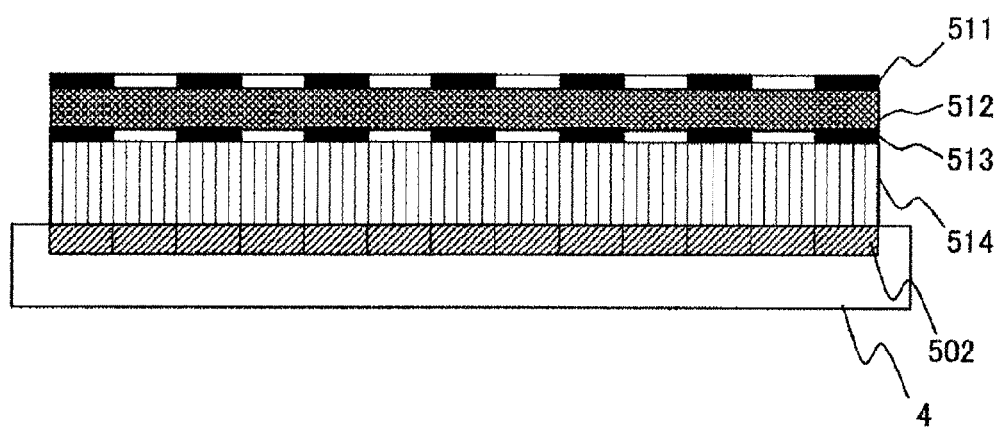
FIG. 10 is a diagram describing the configuration of a high-resolution X-ray TDI camera.

FIG. 10 is a diagram describing the configuration of a high-resolution X-ray TDI camera.

The X-ray TDI camera converts X-rays into visible light with a scintillator and detects the same, but since the light is scattered and blurs are generated in the conversion process thereof, there is the problem that the upper limit of the resolution is restricted to the order of 50 pin. On the top and bottom of a scintillator 512, there are arranged aperture masks 511 and 513 having a resolution that is higher than the upper limit of the scintillator resolution and by guiding the transmitted light thereof to a photoreceptive part with a fiber optic plate 514, blurring due to light scattering in the conversion process is restrained, so a high resolution, at 50 μm or less, can be obtained. The relative positions of aperture mask 511 and aperture mask 513 are adjusted so that the center part of the light beam that is output with scintillator 512, by means of an X-ray beam having passed through each aperture part of aperture mask 511, passes through each of the corresponding aperture parts of aperture mask 513. Further, photoreceptive part 103 of aforementioned X-ray TDI camera 4 corresponds to the input face (being substantially the same as the face of aperture mask 103 in the case of using an aperture mask) of scintillator 512.

Figure 11:
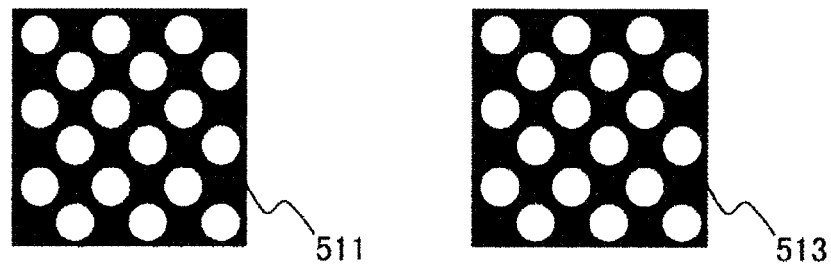
FIG. 11 is a diagram describing aperture masks improving the resolution of a scintillator of an X-ray TDI camera related to the present invention.

FIG. 11 is a diagram describing aperture masks enhancing the resolution of the scintillator of an X-ray TDI camera.

The transmission region has been indicated with white and the shielding region with black. Aperture mask 511 is formed with a quality of material that shields X-rays and the shielding regions of aperture mask 513 are formed with a quality of material that shields light that is output with the scintillator. The more you narrow the individual transmission regions, the higher is the resolution that can be obtained, but if the same are narrowed too much, the aperture ratio (the surface ratio of the transmission regions) diminishes, so the obtainable X-ray fluence diminishes. The example shown in FIG. 11 is one in which transmission regions with a diameter of 25 μm are arranged with a pitch in the x and y directions of 50 μm, so a resolution of 25 μm and an aperture ratio of 39% are obtained. If the present aperture masks are used together with a normal CCD camera or a line scan camera, there is the problem that images of the shielded regions cannot be obtained, but by combining the same with a TDI camera, it is possible to acquire an image of the entire face of the sample with high resolution since, by means of the scanning of the sample, arbitrary regions on the sample mutually pass through shielded regions and transmission regions.

Figure 12:
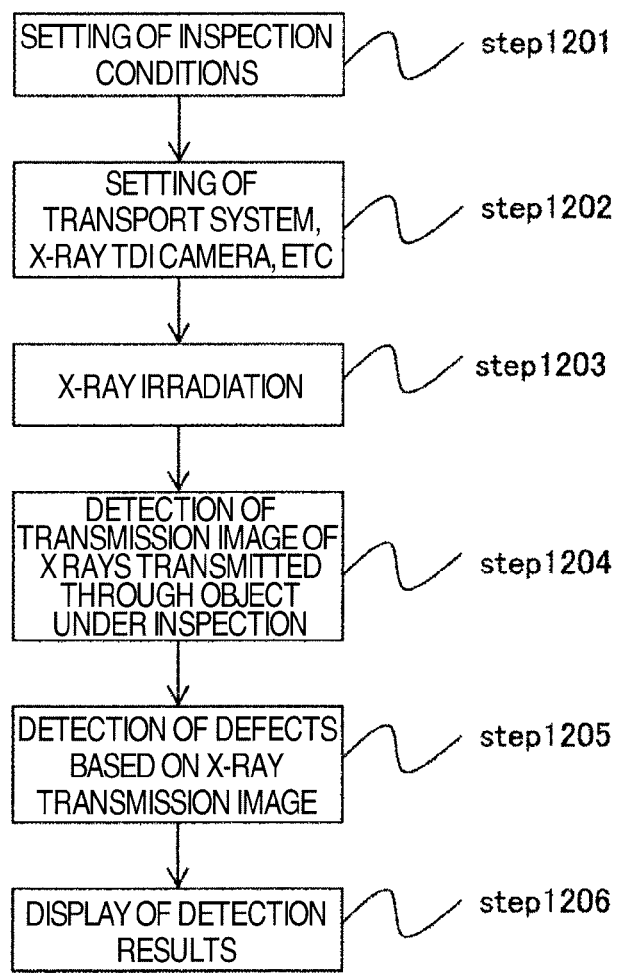
FIG. 12 is a flow diagram for describing an X-ray inspection method related to the present invention.

FIG. 12 is a flow diagram for describing an X-ray scanning method related to the present invention.

A signal pertaining to scanning conditions or the like and received from input part 10 in FIG. 1 or one of the other constituent components is received by control part 8 (Step 1201) and, by means of control part 8, there is carried out setting of conditions of transport system 11, X-ray TDI camera 4, X-ray source 1, and the like (Step 1202). Subsequently, the sample is irradiated with X-rays (Step 1203) by means of X-ray source 1 with the conditions set in Step 1202. The X-rays irradiated on the sample in Step 1203 are transmitted through the sample and X-ray transmission images are detected by means of X-ray TDI camera 4 (Step 1204). Defect judgment part 7 processes the X-ray transmission images detected in Step 1204 and detects defects present in the sample (Step 1205). The defect detection results due to Step 1205 are displayed on display part 9 (Step 1206).

Figure 13:
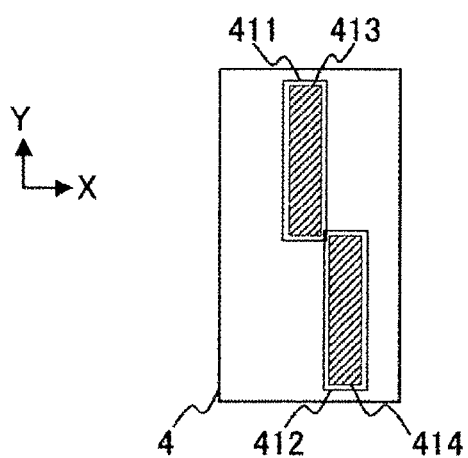
FIG. 13 is a diagram describing the arrangement of photoreceptive sensors of an X-ray TDI camera related to the present invention.

FIG. 13 is a diagram describing the arrangement of photoreceptive sensors of an X-ray TDI camera related to the present invention.

As an X-ray TDI camera 4, there is used one in which there are formed photoreceptive regions that are longer in the y direction, by means of a plurality of photoreceptive sensors 413, 414 that are shifted in the x direction and there is used one that is provided with X-ray tubes corresponding to each of the photoreceptive sensors, so by shifting the x direction positions of a plurality of sample images 411, 412, due to the plurality of X-ray tubes, so that they do not mutually overlap, it is possible to avoid the overlap of images described in FIG. 6.

Further, the present invention is not one limited to the aforementioned embodiments, diverse variations being included therein. E.g., the aforementioned embodiments are ones that have been described in detail in order to comprehensibly describe the present invention, but the invention is not necessarily one limited to ones comprising the entire described configuration. Also, it is possible to substitute a part of the configuration of a certain embodiment in the configuration of another embodiment and, in addition, it is also possible to add to the configuration of a certain embodiment the configuration of another embodiment. Also, regarding a part of the configuration of each embodiment, it is possible to supplement, delete, and substitute other configurations thereto.

Also, as for the control lines and information lines, those considered necessary for the description are indicated, so there are not necessarily indicated all control lines and information lines on the manufactured product. In practice, it may be considered that nearly all of the configurations are interconnected.

REFERENCE SIGNS LIST

1 X-ray source
2 Radiation source shielding part
3 Radiation source slit
4 X-ray TDI camera
5 Direct light shielding part
6 Device cover
7 Defect judgment part
8 Control part
9 Display part

The invention claimed is:

1. An X-ray inspection device, comprising:
an X-ray source irradiating X-rays on a sample;
an X-ray Time Delay Integration (TDI) detector, for detecting X-rays irradiated by said X-ray source and transmitted through said sample as an X-ray transmission image, having a scintillator, an asymmetric fiber optic plate and a square-pixel TDI camera that, in combination, produce flat rectangular detector pixels that are longer in a direction parallel to a scanning direction of said sample, the X-ray TDI detector being arranged adjacent to said sample; and
a defect detection part detecting defects on the basis of X-ray transmission images detected by means of said X-ray TDI detector.

2. The X-ray inspection device according to claim 1, wherein: an amount of blurring of said X-ray transmission images is smaller than a size of the defects detected in said defect detection part.

3. The X-ray inspection device according to claim 1, wherein: the distance between a focal spot of said X-ray source and said X-ray TDI detector is much longer than a distance between said sample and said X-ray TDI detector.

4. The X-ray inspection device according to claim 1, wherein the X-ray source has a focal spot size greater than a defect diameter.

5. The X-ray inspection device according to claim 1, wherein the fiber optic plate is tapered.

6. The X-ray inspection device according to claim 1, wherein the TDI detector further comprises an aperture mask arranged on a top surface of the scintillator and an aperture mask arranged on a bottom surface of the scintillator, the resolution of the top and bottom surface masks being higher than the resolution of the scintillator.

7. An X-ray inspection method, comprising:
irradiating X-rays on a sample using an X-ray source;
detecting X-rays irradiated and transmitted through said sample as an X-ray transmission image using an X-ray TDI detector having a scintillator, an asymmetric fiber optic plate and a square-pixel TDI camera that, in combination, produce flat rectangular detector pixels that are longer in a direction parallel to the scanning direction of said sample, the TDI detector being arranged adjacent to said sample; and
detecting defects on the basis of X-ray transmission images detected.

8. The X-ray inspection method according to claim 7, wherein: an amount of blurring of said X-ray transmission images is smaller than a size of the detected defects.

9. The X-ray inspection method according to claim 7, wherein: a distance between a focal spot of said X-ray source and said X-ray TDI detector is much longer than a distance between said sample and said X-ray TDI detector.

10. The X-ray inspection method according to claim 7, wherein the X-ray source has a focal spot size greater than a defect diameter.

11. The X-ray inspection method according to claim 7, wherein the fiber optic plate is tapered.

12. The X-ray inspection method according to claim 7, wherein the TDI detector further comprises an aperture mask arranged on a top surface of the scintillator and an aperture mask arranged on a bottom surface of the scintillator, the resolution of the top and bottom surface masks being higher than the resolution of the scintillator.

* * * * *